US007790080B2

(12) United States Patent
Huang et al.

(10) Patent No.: US 7,790,080 B2
(45) Date of Patent: Sep. 7, 2010

(54) METHOD FOR FORMING A BIOARTIFICIAL GUIDANCE CONDUIT

(75) Inventors: Yi-You Huang, Taipei (TW); De-Yao Wang, Taipei (TW)

(73) Assignee: National Taiwan University, Taipei (TW)

( * ) Notice: Subject to any disclaimer, the term of this patent is extended or adjusted under 35 U.S.C. 154(b) by 1324 days.

(21) Appl. No.: 11/283,956

(22) Filed: Nov. 22, 2005

(65) Prior Publication Data

US 2007/0118156 A1    May 24, 2007

(51) Int. Cl.
    *B29C 33/40*     (2006.01)
    *B28B 5/00*      (2006.01)
    *B28B 3/06*      (2006.01)
    *A61B 17/08*     (2006.01)
    *A61F 2/00*      (2006.01)

(52) U.S. Cl. .................. 264/227; 264/226; 264/225; 264/219; 264/250; 264/241; 264/297.4; 606/152; 606/151; 424/426; 424/423; 424/422

(58) Field of Classification Search .............. None
    See application file for complete search history.

(56) References Cited

U.S. PATENT DOCUMENTS

| 6,143,293 | A  | * | 11/2000 | Weiss et al. ............. 424/93.7 |
| 6,214,021 | B1 | * | 4/2001  | Hadlock et al. ........... 606/152 |
| 6,365,149 | B2 | * | 4/2002  | Vyakarnam et al. ....... 424/93.1 |
| 6,423,252 | B1 | * | 7/2002  | Chun et al. .............. 264/28 |
| 2002/0127391 | A1 | * | 9/2002  | Kumar ................... 428/325 |
| 2002/0143403 | A1 | * | 10/2002 | Vaidyanathan et al. ... 623/23.51 |
| 2005/0038498 | A1 | * | 2/2005  | Dubrow et al. .......... 623/1.15 |
| 2006/0141012 | A1 | * | 6/2006  | Gingras ................ 424/442 |

FOREIGN PATENT DOCUMENTS

WO    WO 03004254 A1 * 1/2003

OTHER PUBLICATIONS

L. Malaquin, F. Carcenac, C. Vieu, M. Mauzac, Using polydimethylsiloxane as a thermocurable resist for a soft imprint lithography process, Microelectronic Engineering, vols. 61-62, Jul. 2002, pp. 379-384.*

Manhui Sun, Chunxiong Luo, Luping Xu, Hang Ji, Qi Ouyang, Dapeng Yu, and Yong Chen, Artificial Lotus Leaf by Nanocasting, Langmuir, Aug. 16, 2005, vol. 21 (19), pp. 8978-8981.*

Magnus Krogh and Peter Asberg, My Little Guide to Soft Lithography (or Soft Lithography for Dummies), Linkoping University, pp. 1-15.*

J. S. Price, A. F. Tencer, D. M. Arm, G. A. Bohach, Controlled release of antibiotics from coated orthopedic implants, Dec. 6, 1998, vol. 30 (3), pp. 281-286.*

(Continued)

*Primary Examiner*—Christina Johnson
*Assistant Examiner*—Benjamin Schiffman
(74) *Attorney, Agent, or Firm*—WPAT, PC; Justin King

(57) ABSTRACT

The present invention discloses a bioartificial guidance conduit formed by coaxially stacking a plurality of discs and the method for forming the same, wherein each disc contains at least one penetrating hole, and at least one penetrating hole on adjacent discs connects with each other while discs coaxially stacked, so as to run through the formed bioartificial guidance conduit.

45 Claims, 9 Drawing Sheets

OTHER PUBLICATIONS

Tianhong Zhou, Hilel Lewis, Robert E. Foster, Steven P. Schwendeman, Development of a multiple-drug delivery implant for intraocular management of proliferative vitreoretinopathy, Journal of Controlled Release, vol. 55, Issues 2-3, Nov. 13, 1998, pp. 281-295.*

Feng Qian, Norased Nasongkla, Jinming Gao, Membrane-encased polymer millirods for sustained release of 5-fluorouracil, Journal of Biomedical Materials Research Part A, Apr. 19, 2002, vol. 61 (2), pp. 203-211.*

* cited by examiner

METHOD FOR FORMING A BIOARTIFICIAL GUIDANCE CONDUIT

BACKGROUND OF THE INVENTION

1. Field of the Invention

The present invention is generally related to a bioartificial guidance conduit, and more particularly to a bioartificial guidance conduit formed by coaxially stacking and method for forming the same.

2. Description of the Prior Art

In the conventional approach to nerve repair, an attempt is made to align the cut ends of the fascicles (nerve bundles within the nerve trunk). A similar approach is taken with smaller nerves. In either case, the chief hazard to the successful repair is the trauma produced by the manipulation of the nerve ends and the subsequent suturing to maintain alignment. The trauma appears to stimulate the growth and/or migration of fibroblasts and other scar-forming, connective tissue cells. The scar tissue prevents the regenerating axons in the proximal stump from reaching the distal stump to reestablish a nerve charge pathway. The result is a permanent loss of sensory or motor function.

Various attempts have been made over the years to find a replacement for direct (i.e., nerve stump-to-nerve-stump suturing). Much of the research in this field has focused on the use of "channels" or tubular prosthesis which permit the cut ends of the nerve to be gently drawn into proximity and secured in place without undue trauma. It is also generally believed that such channels can also prevent, or at least retard, the infiltration of scar-forming, connective tissue.

Two major conventional fabricating methods of bioartificial guidance conduits are Fiber-Templating and Low-Pressure Injection Molding, and the former is more popular for its high surface area formed by fibers, which is able to facilitate the nerve growth. But it is difficult to control the conformation of fibers, which results in unstable regeneration effect of nerves. Hence, a new bioartificial guidance conduit and its forming method are still needed to produce channels of the conduit with precise dimension, in order to correspond to both economic effect and utilization in industry.

SUMMARY OF THE INVENTION

In accordance with the present invention, a bioartificial guidance conduit and its forming method are provided. This new invention can overcome the drawbacks of the mentioned conventional skill.

One object of the present invention is to employ lithographic process and etching process to fabricate discs with penetrating holes with precise dimension, and so as to provide a new bioartificial guidance conduit fabricating method with high throughput and low cost. Furthermore, the mentioned lithographic process facilitate the forming of microstructure on the wall of the penetrating holes, so as to provide sufficient growing space for Schwann cells and nerve adherence. Therefore, Schwann cells are seeded in microstructures and along the conduit.

Another object of the present invention is to choose proper cross-sectional shape of the bioartificial guidance conduit, so as to coaxially stack the discs from some specific orientations. Therefore, precisely match between penetrating holes on the same relative position of each disc can be achieved while discs coaxially stacked, and the bioartificial guidance conduit is formed with passable channel(s). Still another object of the present invention is to control the decomposing rate of said disc located at the middle of said bioartificial guidance conduit being slower than the decomposing rate of said disc located at the two ends of said bioartificial guidance conduit, so as to accelerating the bulk decomposing rate of the conduit. Hence, this present invention does have the economic advantages for industrial applications.

Accordingly, the present invention discloses a bioartificial guidance conduit formed by coaxially stacking a plurality of discs and the method for forming the same, wherein each disc contains at least one penetrating hole, and at least one penetrating hole on adjacent discs connects with each other while discs coaxially stacked, so as to run through the formed bioartificial guidance conduit.

DESCRIPTION OF THE PREFERRED EMBODIMENTS

What is probed into the invention is a composite membrane containing PTFE and a method for forming the same. Detail descriptions of the structure and elements will be provided in the following in order to make the invention thoroughly understood. Obviously, the application of the invention is not confined to specific details familiar to those who are skilled in the art. On the other hand, the common structures and elements that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

Figure 1A:
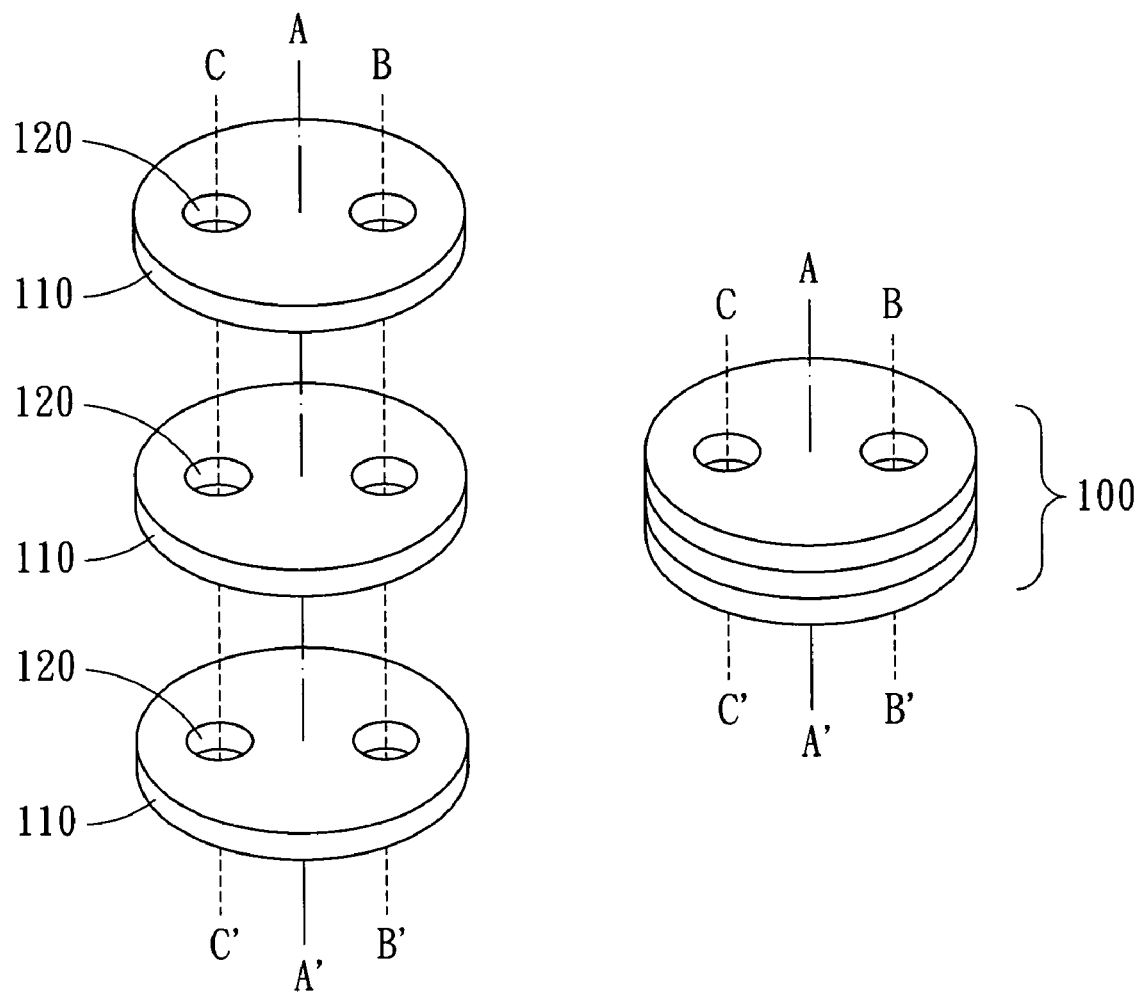
FIG. 1A is a three dimensional view of a bioartificial guidance conduit formed by coaxially stacking according to the first embodiment of the present invention.
Figure 1B:
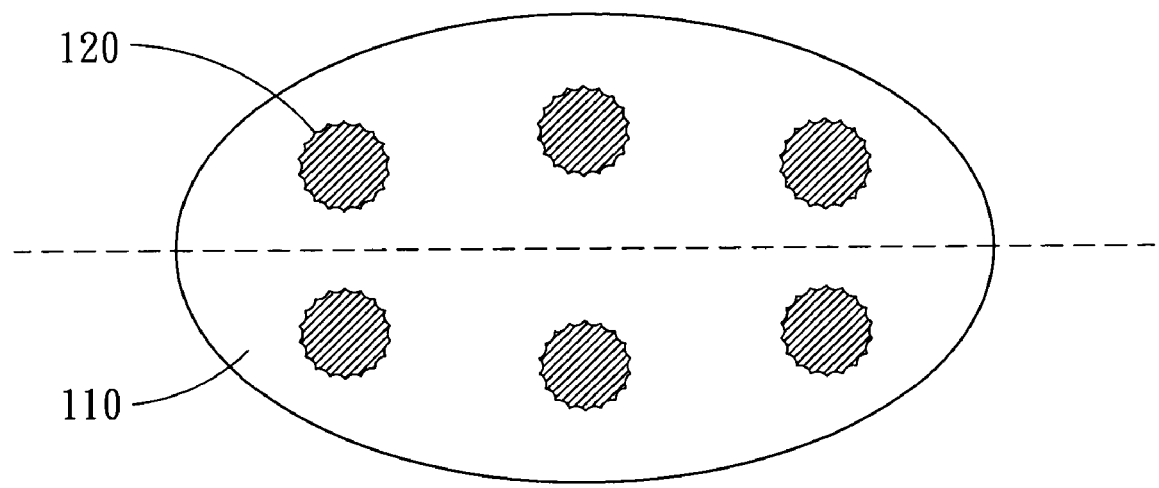
FIG. 1B is a cross-sectional view of the microstructures on the wall of the penetrating holes according to the first embodiment of the present invention.

In a first embodiment of the present invention, a bioartificial guidance conduit with cross-sectional area from $1\ mm^2$ to $25\ mm^2$ is provided. The bioartificial guidance conduit is formed by coaxially stacking a plurality of discs with thickness from 10 μm to 500 μm, wherein each disc contains at least one penetrating hole, and at least one penetrating hole on adjacent discs connects with each other while discs coaxially stacked, so as to run through the formed bioartificial guidance conduit. Referring to FIG. 1A, in a preferred example of this embodiment, three discs 110 are stacked along the central axis A-A' to form the bioartificial guidance conduit 100, wherein each disc 110 comprises two penetrating holes 120, and along B-B' and C-C', penetrating holes 120 on the same relative position of each disc are aligned respectively. Additionally, the wall of the penetrating holes can be designed with microstructures, such as: dents, grooves, denticulate structures, so as to provide sufficient growing space for Schwann cells. Therefore, Schwann cells are seeded in microstructures and along the conduit. Chemical functional groups can be further patterned inside the conduits for selective Schwann cell and nerve adherence. Due to the cooperation of several neural trophic factors (NTFs) secreted by Schwann cells and possibly, the effect of extracelluar matrix (ECM) and cell adhension molecules (CAM) as well. And the Schwann cell can provide biological effect on the nerve growth. Then, nerve regeneration and growth along the physical orientation is provided by conduits. As shown in FIG. 1B, in another preferred example of this embodiment, the wall of the penetrating holes 120 located in the disc 110 comprises denticulate structures. In summery, the bioarticifial guidance conduit with microstructures gives physical, chemical, and cellular guidance cues to promote nerve regeneration at the cellular level.

Figure 1C:
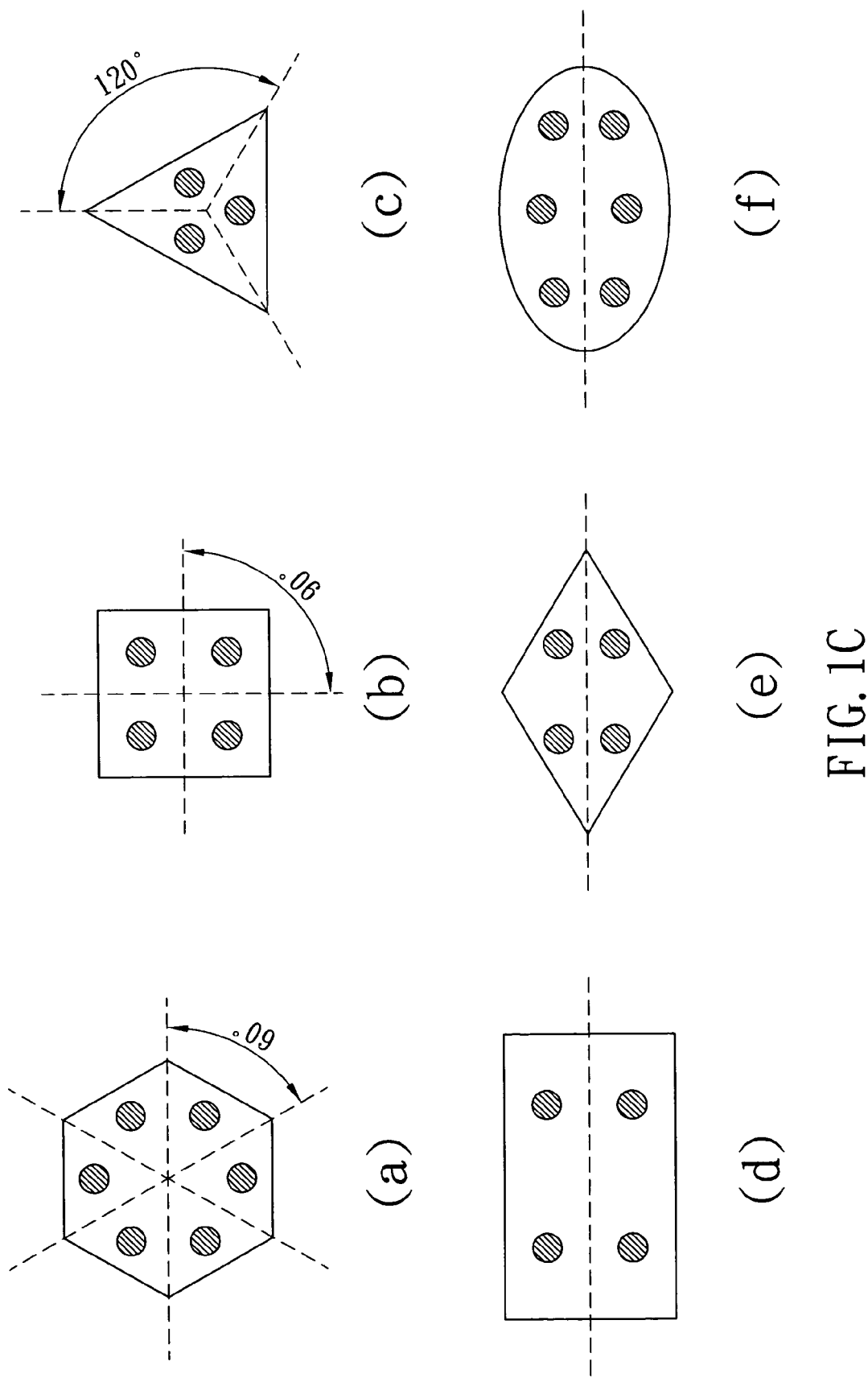
FIG. 1C is a cross-sectional view of the cross-sectional shape of discs, and the penetrating holes on the same disc have different symmetry according to the first embodiment of the present invention.

In this embodiment, the preferred cross-sectional shape of the bioartificial guidance conduit is not perfect circle, so as to coaxially stack the discs from some specific orientations. Therefore, precisely match between penetrating holes on the same relative position of each disc can be achieved while discs coaxially stacked, and the bioartificial guidance conduit is formed with passable channel(s). Referring to FIG. 1C, the present invention discloses some cross-sectional shape for discs, wherein (a) the cross-sectional shape is regular hexagon, and the penetrating holes on the same disc have rotational symmetry with respect to an angle of 60° (b) the cross-sectional shape is square, and the penetrating holes on the same disc have rotational symmetry with respect to an angle of 90° (c) the cross-sectional shape is equilateral triangle, and the penetrating holes on the same disc have rotational symmetry with respect to an angle of 120°. Furthermore, when the cross-sectional shape is rectangle, rhombus, or ellipse respectively in (d) (e) (f), the penetrating holes on the same disc have reflection or mirror symmetry. Among the above-mentioned different cross-sectional shapes of discs, shape with reflection or mirror symmetry is more preferred for giving much flexibility to the positions of the penetrating holes. Additionally, ellipse is the most preferred cross-sectional shape, wherein the length of major axis and minor axis of the ellipse ranges from 1 mm to 5 mm. One advantage of this design is to reducing the defects in the disk production process, so as to achieve the greatest economic efficiency.

In this embodiment, the material of the disc is selected as any one or any combination of the following group: chitosan, poly(lactic acid), poly(glycolic acid) [PGA], poly(glycolide co-lactide) [PLGA], collage, polycarboxylic acid, alginate, polyamide and their derivatives. Additionally, in still another preferred example, the decomposing rate of said disc located at the middle of said bioartificial guidance conduit is slower than the decomposing rate of said disc located at the two ends of said bioartificial guidance conduit. Therefore, the conduit will decompose from ends to the center, and nerve regeneration and growth are also from ends to the center of the conduit. This design is able to accelerating the bulk decomposing rate of the conduit. Moreover, decomposing rate is varied by selecting different materials or controlling the porosity of the discs.

In this embodiment, the bioartificial guidance conduit further comprises a shell to cover said bioartificial guidance conduit, so as to increase mechanical strength of the bioartificial guidance conduit, or to fix the coaxially stacked discs. Besides, structure of the shell can be porous, dense, or semipermeable. Moreover, material of said shell is selected as any one or any combination of the following group: chitosan, poly(lactic acid), poly(glycolic acid) [PGA], poly(glycolide co-lactide) [PLGA], collage, polycarboxylic acid, alginate, polyamide and their derivatives.

Figure 2A:
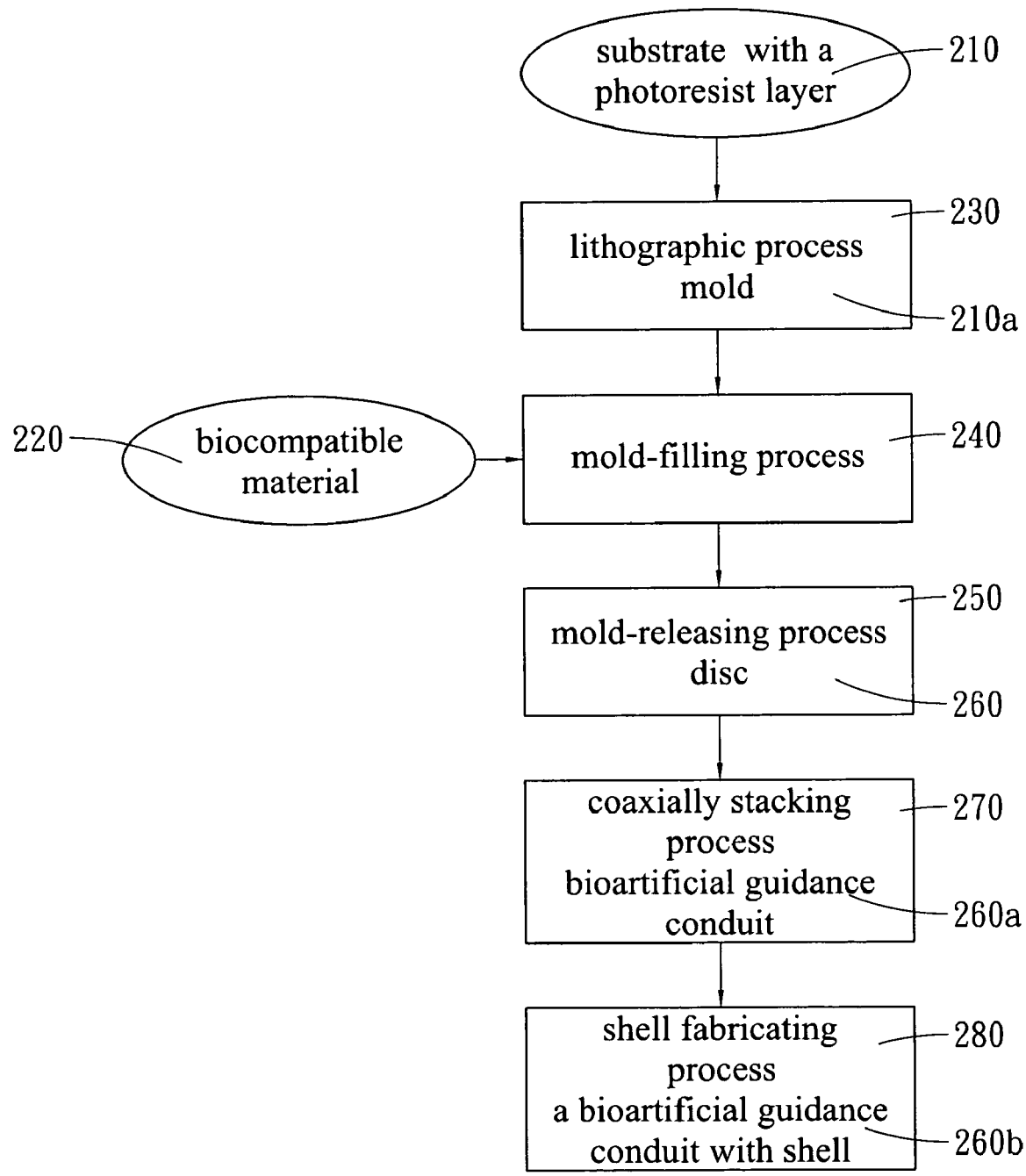
FIG. 2A is a flow chart of a method for forming bioartificial guidance conduit in accordance with the second embodiment of the present invention.
Figure 2B:
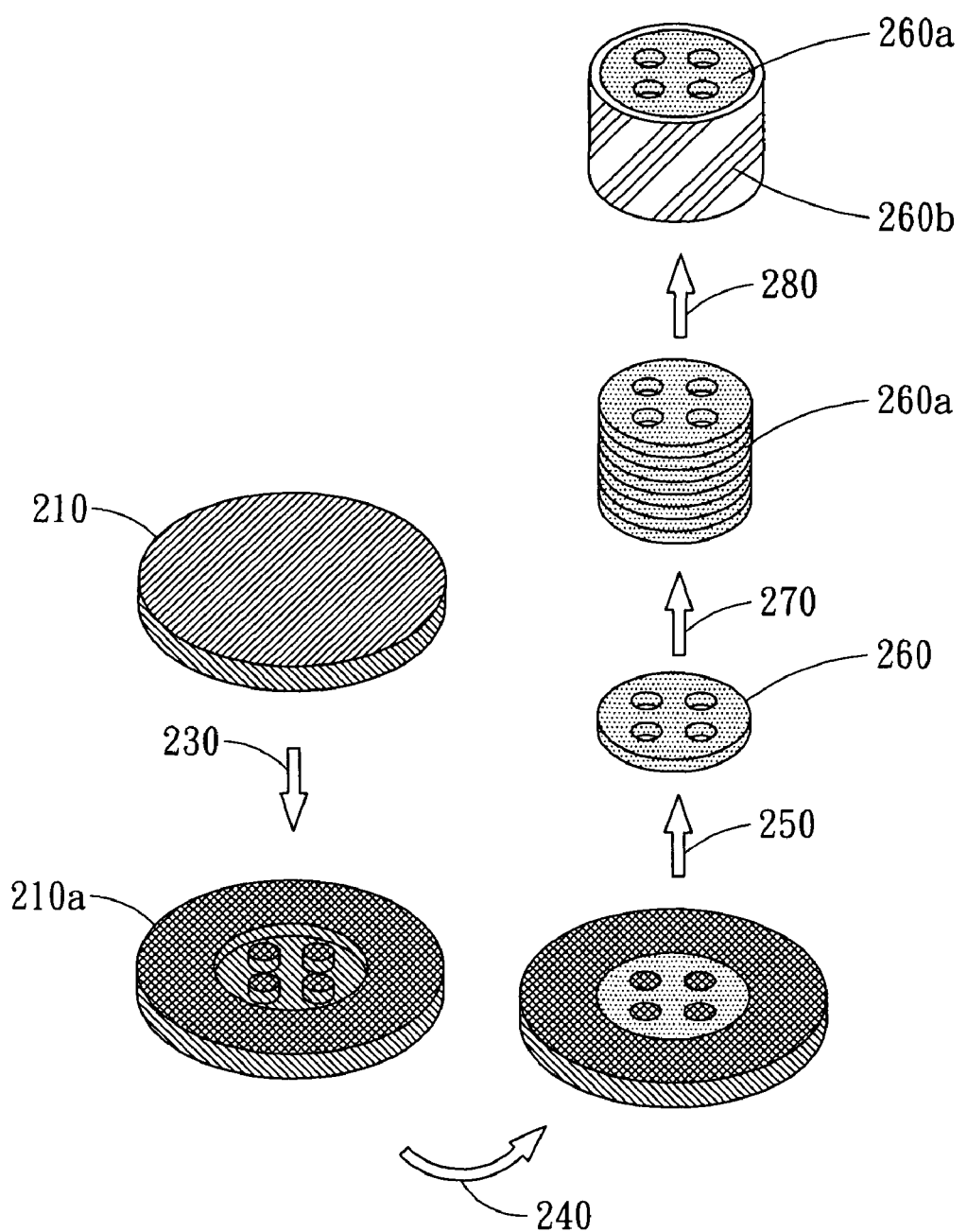
FIG. 2B is a schematic diagram of a method for forming bioartificial guidance conduit in accordance with the second embodiment of the present invention.

As shown in FIG. 2A and FIG. 2B, in a second embodiment of the present invention, a method for forming a bioartificial guidance conduit is disclosed. First, a substrate with a photoresist layer 210 is provided, and then a lithographic process 230 is performed on said photoresist layer to form a mold 210a that comprises at least one first pattern having a flat-bottom cave and at least one second pattern having a plurality of pillar-shaped structures extending from said flat-bottom cave, wherein the depth of said flat-bottom cave is substantially equal to the height of said pillar-shaped structure. In a preferred example of this embodiment, the first pattern is formed by etching through said substrate during said lithographic process 230, and a connecting structure is formed to connect said substrate with said second pattern during said lithographic process 230. After the lithographic process 230, a mold-filling process 240 is performed to fill said mold 210a with a biocompatible material 220, so as to form at least one disc 260 with thickness from 10 μm to 500 μm and cross-sectional area from 1 mm² to 25 mm², wherein the main body of said disc 260 is formed by said first pattern, and at least one penetrating hole with cross-sectional area from 100 μm² to 10⁶ μm² of said disc 260 is formed by said second pattern. In addition, the material of said disc 260 is selected as any one or any combination of the following group: chitosan, poly(lactic acid), poly(glycolic acid) [PGA], poly(glycolide co-lactide) [PLGA], collage, polycarboxylic acid, alginate, polyamide and their derivatives. Next, a mold-releasing process 250 is performed to take out at least one said disc 260. Subsequently, the mold-filling process 240 and said mold-releasing process 250 are repeated sequentially to produce a plurality of said discs 260. Finally, a coaxially stacking process 270 is performed to stack said plurality of discs 260, and the bioartificial guidance conduit 260a is then formed, wherein at least one said penetrating hole on adjacent said plurality of discs 260 connects with each other, so as to run through said bioartificial guidance conduit 260a.

In this embodiment, the preferred cross-sectional shape of said bioartificial guidance conduit 260a is not perfect circle, Detail consideration about the cross-sectional shape has been described in the first embodiment. In another preferred example of this embodiment, the cross-sectional shape of said bioartificial guidance conduit 260a is ellipse, wherein the length of major axis and minor axis of the ellipse ranges from 1 mm to 5 mm. Additionally, after the bioartificial guidance conduit 260a is formed, a shell fabricating process 280 is performed to form a shell; so as to cover said coaxially stacked plurality of discs 260. Besides, the material of said shell is selected as any one or any combination of the following group: chitosan, poly(lactic acid), poly(glycolic acid) [PGA], poly(glycolide co-lactide) [PLGA], collage, polycarboxylic acid, alginate, polyamide and their derivatives. Furthermore, one procedure of the shell fabricating process 280 is as following: a solution is coated onto the outer surface of said coaxially stacked plurality of discs 260, wherein said solution comprises a biocompatible material. With proper viscosity, the solution is able to cover uniformly and completely onto the coaxially stacked discs 260. Afterwards, a drying process is performed to gel said solution located on said coaxially stacked plurality of discs, and a bioartificial guidance conduit with shell 260b is then formed. Another procedure of the shell fabricating process 280 is as following: a solution is coated onto the outer surface of said coaxially stacked plurality of discs to form an intermediate conduit, wherein said solution comprises a biocompatible material. With proper viscosity, the solution is able to cover uniformly and completely onto the coaxially stacked discs 260. Afterwards, a phase separation process is performed to soak said intermediate conduit into a nonsolvent, so as to gel said solution located on said coaxially stacked plurality of discs 260, and a bioartificial guidance conduit with shell 260b is then formed. Still another procedure of the shell fabricating process 280 is as following: a plate-shaped biocompatible material is provided. Next, the plate-shaped biocompatible material is wrapped around said coaxially stacked plurality of discs 260. Then, a binding process is performed to connect the outer surface of said coaxially stacked plurality of discs 260 with said plate-shaped biocompatible material, so as to form a bioartificial guidance conduit with shell 260b.

Figure 3A:
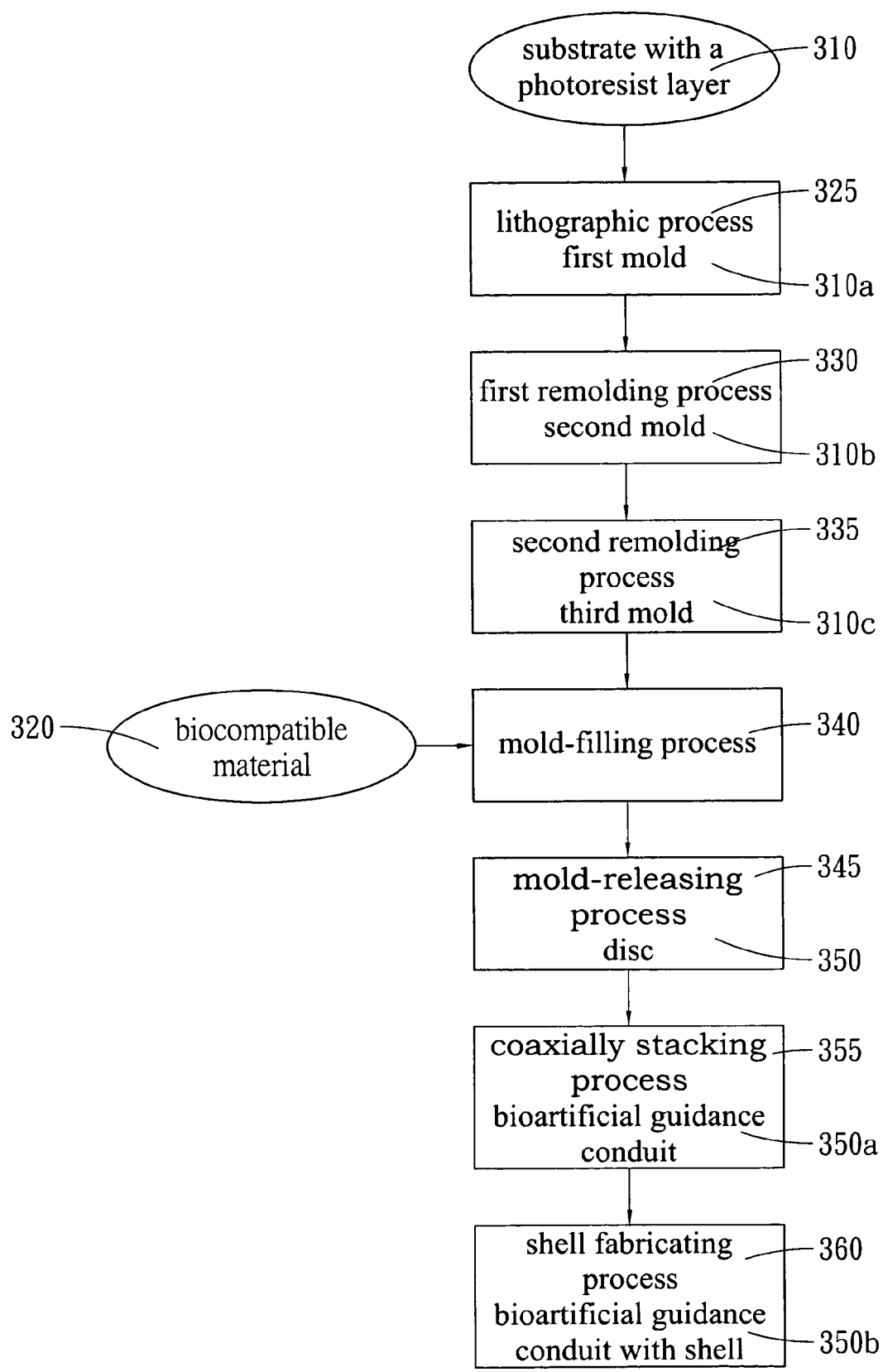
FIG. 3A is a flow chart of a method for forming bioartificial guidance conduit in accordance with the third embodiment of the present invention.
Figure 3B:
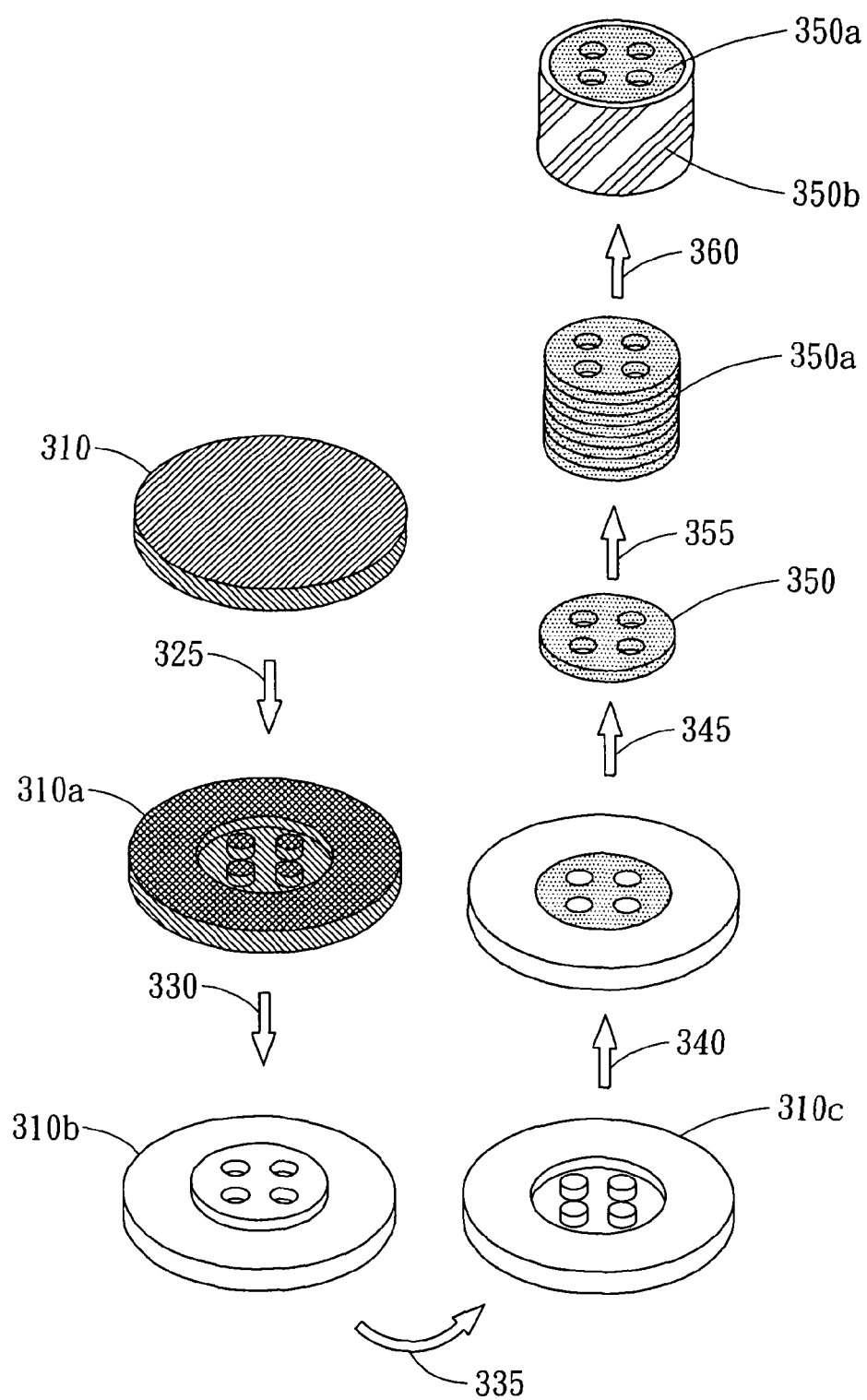
FIG. 3B is a schematic diagram of a method for forming bioartificial guidance conduit in accordance with the third embodiment of the present invention.

As shown in FIG. 3A and FIG. 3B, in a third embodiment of the present invention, a method for forming a bioartificial guidance conduit is disclosed. First, a substrate with a photoresist layer 310 is provided, and then a lithographic process 325 is performed on said photoresist layer to form a first mold 310a that comprises at least one first pattern having a flat-bottom cave and at least one second pattern having a plurality of pillar-shaped structures extending from said flat-bottom cave, the depth of said flat-bottom cave is substantially equal to the height of said pillar-shaped structure. In a preferred example of this embodiment, the first pattern is formed by etching through said substrate during said lithographic process 325, and a connecting structure is formed to connect said substrate with said second pattern during said lithographic process 325. After the lithographic process 325, a first remolding process 330 is performed by said first mold 310a and a first flexible material to fabricate a second mold 310b. Next, a second remolding process 335 by said second mold 310b and a second flexible material to fabricate a third mold 310c, wherein said third mold 310c comprises substantially the same said first pattern and said second pattern. The first flexible material and said second flexible material are independently selected from the following group: poly(dimethyl siloxane) [PDMS], polyurethane. When the first flexible material and said second flexible material are the same, a surface modification process is performed to modify the surface of said second mold with hydrophobic property. Therefore, the third mold can be easily taken off from the second mold.

In this embodiment, after the second remolding process 335, a mold-filling process 340 to fill said third mold 310c with a biocompatible material 320, so as to form at least one disc 350, wherein the main body of said disc 350 is formed by said first pattern, and at least one penetrating hole of said disc 350 is formed by said second pattern. The biocompatible material 320 is the same as that of the second embodiment. Next, a mold-releasing process 345 is performed to take out at least one disc 350. Subsequently, the mold-filling process 340 and said mold-releasing process 345 are repeated sequentially to produce a plurality of said discs 350. Finally, a coaxially stacking process 355 is performed to stack said plurality of discs 350, and the bioartificial guidance conduit 350a is then formed, wherein at least one said penetrating hole on adjacent said plurality of discs 350 connects with each other, so as to run through said bioartificial guidance conduit 350a. Additionally, after the bioartificial guidance conduit 350a is formed, a shell fabricating process 360 is performed to form a shell; so as to cover said coaxially stacked plurality of discs 350, and a bioartificial guidance conduit with shell 350b is then formed. Besides, the material of said shell and detail procedure of shell fabricating process 360 are the same as those of the second embodiment.

EXAMPLE

Photomask Production

Pattern of 20×20 cross-sectional shapes of penetrating holes is generated by a LASER-beam pattern generator, and a photomask of quartz blank imprinted with the mentioned pattern defined with chrome metal is sequentially formed, wherein the cross-sectional shape is ellipse and the region thereof is transparent. Furthermore, the wall of the penetrating holes can be designed with microstructures, such as: denticulate structure, so as to enhance the guidance effect and provide sufficient growing space for Schwann cell.

Lithographic Process

First, a 4-inch silicon-wafer is washed and then dehydrated in150-200° C. at vacuum or dehydrated nitrogen. Next, photoresist SU-8 is applied to define the pattern on the wafer and a negative photoresist. After dispensing suitable amount of photoresist onto the wafer, the spin coater was ramped to 2000-6000 rpm and the formed photoresist layer is about 50-100 μm. The adhesive property between photoresist and wafer can be increased by introducing hexamethyldisilazane. The wafer is first coated with hexamethyldisilazane, and photoresist is subquentially applied thereon. Therefore, one end of hexamethyldisilazane is bound to the wafer, and the other end of hexamethyldisilazane is bound to the photoresist. Afterwards, soft baking at 90-100° C. for 30 seconds to 30 minutes is used to evaporate solvents from the photoresist, so as to reduce the concentration of solvent to 5% of the original concentration. Then, exposure is performed to harden the exposed region of SU-8, followed by washing off the unexposed region of SU-8 (cross-sectional shapes of penetrating holes), so as to form a SU-8 mask with the mentioned pattern. After the exposure, hard baking at 90-120° C. is used to increase the adhesive property and anti-etching ability of the SU-8 mask.

Etching Process (First Mold Production)

Selectivity is the ratio of the etch rates of two different materials. It can also be accomplished using plasma etching. Patterning a sample requires minimal erosion of the mask and considerable erosion (etching) of the sample; thus, high selectivity between the two materials is required. Anisotropy is defined as the vertical etch rate divided by the horizontal etch rate. Therefore, trench with high anisotropic aspect ratio can be formed by Inductive Coupling Plasma Etching (ICP). The plasma etching selectivity ratio to SU-8 mask and silicon wafer ranges from 1:3 to 1:20, whereupon the depth of the formed trench is about 300-400 μm. Conventional etching process is usually followed by removing photoresist mask (such as: SU-8 mask) by acetone or sulfuric acid-hydrogen peroxide, but this invention doesn't remove the SU-8 mask, in order to increase the depth of the penetrating hole to 400-500 μm (300-400 μm from the depth of trench plus 50-100 μm from the SU-8 mask).

Second Mold Production

The first mold is filled with PDMS, and curing at 65° C. for 4 hours. Then, a mold-releasing process is performed to take out a second mold from the first mold.

Third Mold Production

A surface modification process is performed by $CF_4/H_2$ or $CHF_3$ plasma to modify the surface of the second mold with hydrophobic property. The modified second mold is filled with PDMS, and then curing at 65° C. for 4 hours.

Disc Production

A mold-filling process is performed to fill the third mold with chitosan or polyurethane, so as to form a disc with the pattern of 20×20 cross-sectional shapes of penetrating holes. Next, a mold-releasing process is performed to take out the disc. Afterwards, repeating said mold-filling process and said mold-releasing process to produce a plurality of the discs.

Bioartificial Guidance Conduit Production

Because the cross-sectional shape of disc is ellipse, the discs can be stacked only from two specific orientations. Therefore, a coaxially stacking process is performed to stack the discs, so as to form said bioartificial guidance conduit, wherein 20×20 penetrating holes on adjacent discs connects with each other, so as to run through said bioartificial guidance conduit.

Figure 4A:
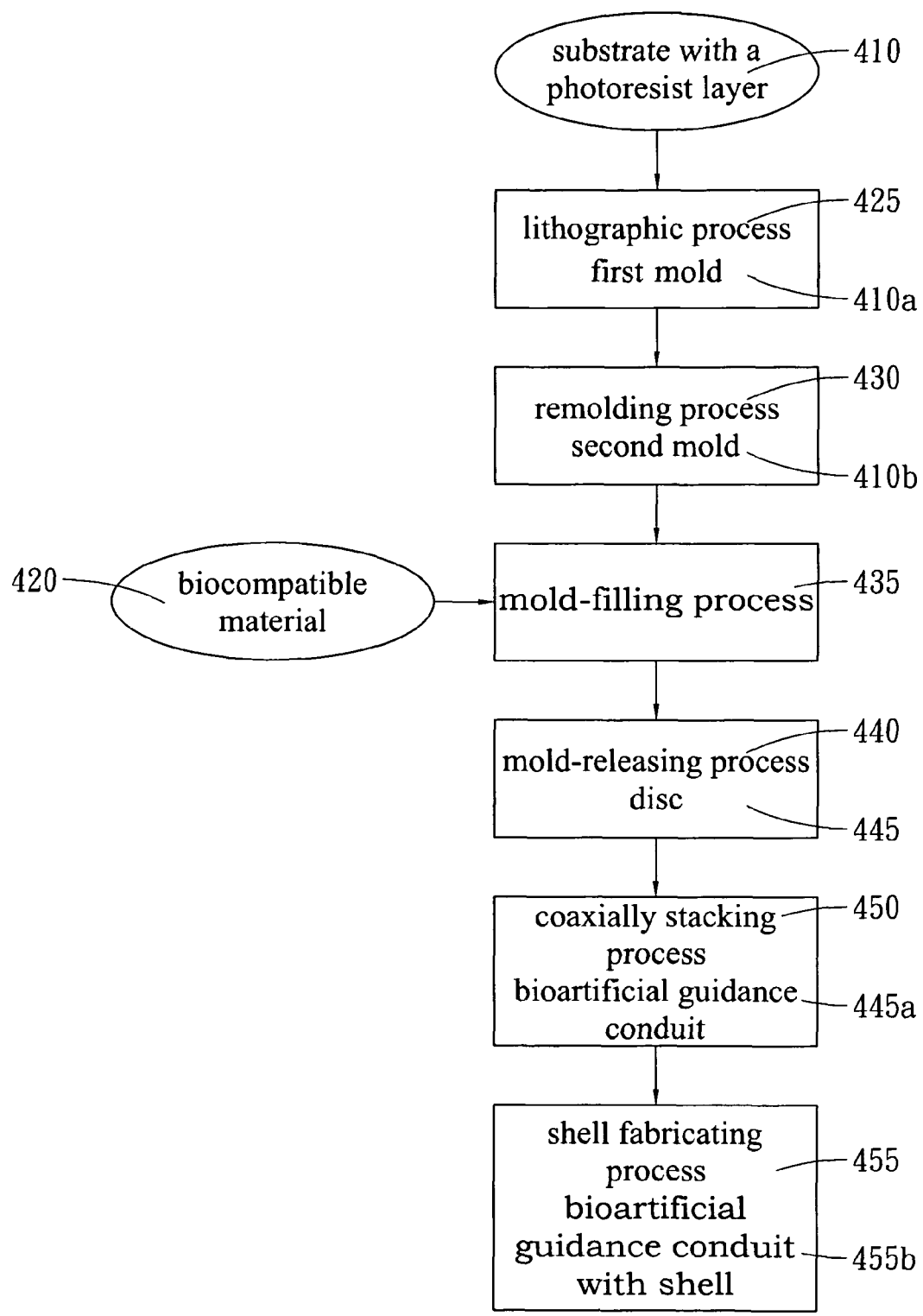
FIG. 4A is a flow chart of a method for forming bioartificial guidance conduit in accordance with the fourth embodiment of the present invention.
Figure 4B:
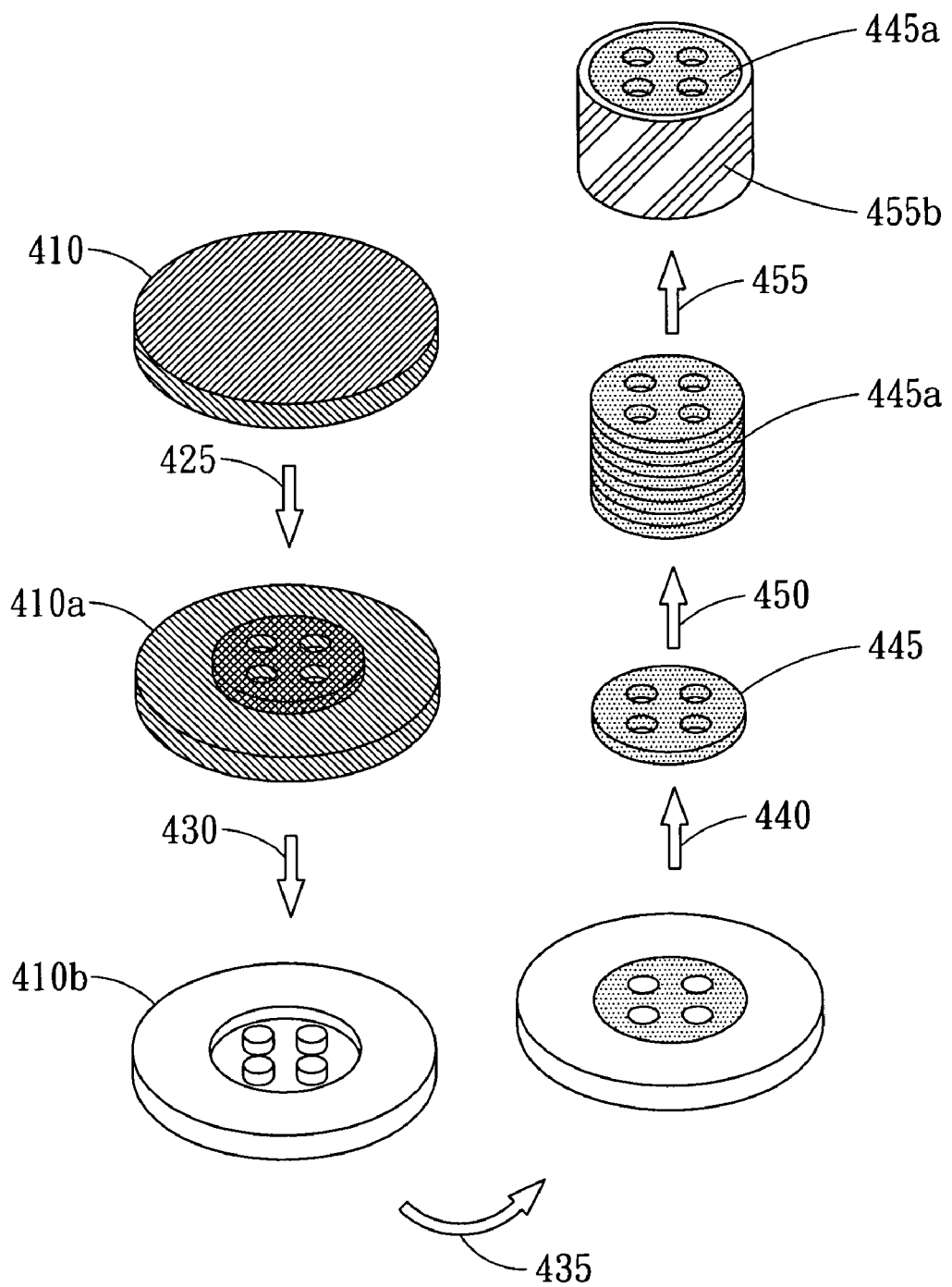
FIG. 4B is a schematic diagram of a method for forming bioartificial guidance conduit in accordance with the fourth embodiment of the present invention.

As shown in FIG. 4A and FIG. 4B, in a fourth embodiment of the present invention, a method for forming a bioartificial guidance conduit is disclosed. First, a substrate with a photoresist layer 410 is provided, and then a lithographic process 425 is performed on said photoresist layer to form a first mold 410a that comprises at least one first pattern having a raised flat-top structure and at least one second pattern having a plurality of tubular holes extending into said substrate from said raised flat-top structure, wherein the height of said raised flat-top structure is substantially equal to the depth of said tubular hole. Next, a remolding process 430 is performed by said first mold 410a and a flexible material to fabricate a second mold 410b, wherein said second mold 410b comprises a third pattern complementary to said first pattern and a fourth pattern complementary to said second pattern, and the height of said third pattern is substantially equal to the height of said fourth pattern. The mentioned flexible material is selected from the following group: poly(dimethyl siloxane) [PDMS], polyurethane. After the remolding process 430, a mold-filling process 435 is performed to fill said second mold 410b with a biocompatible material 420, so as to form at least one disc 445, wherein the main body of said disc 445 is formed by said third pattern, and at least one penetrating hole of said disc 445 is formed by said fourth pattern. The biocompatible material 420 is the same as that of the second embodiment. Then, a mold-releasing process 440 is performed to take out at least one said disc 445. Subsequently, the mold-filling process 435 and said mold-releasing process 440 are repeated sequentially to produce a plurality of said discs 445. Finally, a coaxially stacking process 450 is performed to stack said plurality of discs 445, and the bioartificial guidance conduit 445a is then formed, wherein at least one said penetrating hole on adjacent said plurality of discs 445 connects with each other, so as to run through said bioartificial guidance conduit 445a. Additionally, after the bioartificial guidance conduit 445a is formed, a shell fabricating process 455 is performed to form a shell; so as to cover said coaxially stacked plurality of discs 445, and a bioartificial guidance conduit with shell 445b is then formed. Besides, the material of said shell and detail procedure of shell fabricating process 455 are the same as those of the second embodiment.

In the above preferred embodiments, the present invention employs lithographic process and etching process to fabricate discs with penetrating holes with precise dimension, and so as to provide a new bioartificial guidance conduit fabricating method with high throughput and low cost. Furthermore, the mentioned lithographic process facilitate the forming of microstructure on the wall of the penetrating holes, so as to provide sufficient growing space for Schwann cells and nerve adherence. Therefore, Schwann cells are seeded in microstructures and along the conduit. Additionally, this invention discloses how to choose proper cross-sectional shape of the bioartificial guidance conduit, so as to coaxially stack the discs from some specific orientations. Therefore, precisely match between penetrating holes on the same relative position of each disc can be achieved while discs coaxially stacked, and the bioartificial guidance conduit is formed with passable channel(s). Hence, this present invention does have the economic advantages for industrial applications.

To sum up, the present invention discloses a bioartificial guidance conduit formed by coaxially stacking a plurality of discs and the method for forming the same, wherein each disc contains at least one penetrating hole, and at least one penetrating hole on adjacent discs connects with each other while discs coaxially stacked, so as to run through the formed bioartificial guidance conduit.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A method for forming a bioartificial guidance conduit, comprising:

providing a substrate with a photoresist layer;

performing a lithographic process on said photoresist layer to form a mold that comprises at least one first pattern having a flat-bottom cave and at least one second pattern having a plurality of pillar-shaped structures extending from said flat-bottom cave, wherein the depth of said flat-bottom cave is substantially equal to the height of said pillar-shaped structure;

performing a mold-filling process to fill said mold with a biocompatible material, so as to form at least one disc, wherein the main body of said disc is formed by said first pattern, and at least one penetrating hole of said disc is formed by said second pattern;

performing a mold-releasing process to take out at least one said disc; repeating said mold-filling process and said mold-releasing process to produce a plurality of said discs; and performing a coaxially stacking process to stack said plurality of discs, and said bioartificial guidance conduit is then formed, wherein at least one said penetrating hole on adjacent said plurality of discs connects with each other, so as to run through said bioartificial guidance conduit, wherein the decomposing rate of said disc located at the middle of said bioartificial guidance conduit being slower than the decomposing rate of said disc located at the two ends of said bioartificial guidance conduit.

2. The method for forming a bioartificial guidance conduit in claim 1, wherein said first pattern is formed by etching through said substrate during said lithographic process, and a connecting structure is formed to connect said substrate with said second pattern during said lithographic process.

3. The method for forming a bioartificial guidance conduit in claim 1, wherein the material of said disc is selected as any one or any combination of the following group: chitosan, poly (lactic acid), poly (glycolic acid) [PGA], poly (glycolide co-lactide) [PLGA], collage, polycarboxylic acid, alginate, polyamide and their derivatives.

4. The method for forming a bioartificial guidance conduit in claim 1, wherein the thickness of said disc ranges from 10 μm to 500 μm.

5. The method for forming a bioartificial guidance conduit in claim 1, wherein the cross-sectional area of said bioartificial guidance conduit ranges from 1 mm2 to 25 mm2.

6. The method for forming a bioartificial guidance conduit in claim 1, wherein the cross-sectional shape of said bioartificial guidance conduit is not perfect circle.

7. The method for forming a bioartificial guidance conduit in claim 1, wherein the cross-sectional shape of said bioartificial guidance conduit is ellipse.

8. The method for forming a bioartificial guidance conduit in claim 7, wherein the length of major axis and minor axis of the ellipse ranges from 1 mm to 5 mm.

9. The method for forming a bioartificial guidance conduit in claim 1, wherein the cross sectional area of said penetrating hole ranges from 100 μm2 to 106 μm2.

10. The method for forming a bioartificial guidance conduit in claim 1, further comprising a shell fabricating process to form a shell, so as to cover said coaxially stacked plurality of discs.

11. The method for forming a bioartificial guidance conduit in claim 10, wherein the method for fabricating said shell comprises:
    coating a solution onto the outer surface of said coaxially stacked plurality of discs, wherein said solution comprises a biocompatible material; and
    performing a drying process to gel said solution located on said coaxially stacked plurality of discs, and said shell is then formed.

12. The method for forming a bioartificial guidance conduit in claim 10, wherein the method for fabricating said shell comprises:
    coating a solution onto the outer surface of said coaxially stacked plurality of discs to form an intermediate conduit, wherein said solution comprises a biocompatible material; and
    performing a phase separation process to soak said intermediate conduit into a nonsolvent, so as to gel said solution located on said coaxially stacked plurality of discs, and said shell is then formed.

13. The method for forming a bioartificial guidance conduit in claim 10, wherein the method for fabricating said shell comprises:
    providing a plate-shaped biocompatible material;
    wrapping said plate-shaped biocompatible material around said coaxially stacked plurality of discs; and
    performing a binding process to connect the outer surface of said coaxially stacked plurality of discs with said plate-shaped biocompatible material, so as to form said shell.

14. The method for forming a bioartificial guidance conduit in claim 10, wherein the material of said shell is selected as any one or any combination of the following group: chitosan, poly (lactic acid), poly (glycolic acid) [PGA], poly (glycolide co-lactide) [PLGA], collage, polycarboxylic acid, alginate, polyamide and their derivatives.

15. A method for forming a bioartificial guidance conduit, comprising:
    providing a substrate with a photoresist layer;
    performing a lithographic process on said photoresist layer to form a first mold that comprises at least one first pattern having a flat-bottom cave and at least one second pattern having a plurality of pillar-shaped structures extending from said flat-bottom cave, the depth of said flat-bottom cave is substantially equal to the height of said pillar-shaped structure;
    performing a first remolding process by said first mold and a first flexible material to fabricate a second mold;
    performing a second remolding process by said second mold and a second flexible material to fabricate a third mold, wherein said third mold comprises substantially the same said first pattern and said second pattern;
    performing a mold-filling process to fill said third mold with a biocompatible material, so as to form at least one disc, wherein the main body of said disc is formed by said first pattern, and at least one penetrating hole of said disc is formed by said second pattern;
    performing a mold-releasing process to take out at least one said disc;
    repeating said mold-filling process and said mold-releasing process to produce a plurality of said discs; and
    performing a coaxially stacking process to stack said plurality of discs, so as to form said bioartificial guidance conduit, wherein at least one said penetrating hole on adjacent said plurality of discs connects with each other, so as to run through said bioartificial guidance conduit, wherein the decomposing rate of said disc located at the middle of said bioartificial guidance conduit being slower than the decomposing rate of said disc located at the two ends of said bioartificial guidance conduit.

16. The method for forming a bioartificial guidance conduit in claim 15, wherein said first pattern is formed by etching through said substrate during said lithographic process, and a connecting structure is formed to connect said substrate with said second pattern during said lithographic process.

17. The method for forming a bioartificial guidance conduit in claim 15, wherein said first flexible material and said second flexible material are independently selected from the following group: poly(dimethyl siloxane) [PDMS], polyurethane.

18. The method for forming a bioartificial guidance conduit in claim 15, wherein said first flexible material and said second flexible material are the same.

19. The method for forming a bioartificial guidance conduit in claim 18, further comprising a surface modification process, performed after said first remolding process, to modify the surface of said second mold with hydrophobic property.

20. The method for forming a bioartificial guidance conduit in claim 15, wherein the material of said biocompatible material is selected as any one or any combination of the following group: chitosan, poly (lactic acid), poly (glycolic acid) [PGA], poly (glycolide co-lactide) [PLGA], collage, polycarboxylic acid, alginate, polyamide and their derivatives.

21. The method for forming a bioartificial guidance conduit in claim 15, wherein the thickness of said disc ranges from 10 μm to 500 μm.

22. The method for forming a bioartificial guidance conduit in claim 15, wherein the cross-sectional area of said bioartificial guidance conduit ranges from 1 mm2 to 25 mm2.

23. The method for forming a bioartificial guidance conduit in claim 15, wherein the cross-sectional shape of said bioartificial guidance conduit is not perfect circle.

24. The method for forming a bioartificial guidance conduit in claim 15, wherein the cross-sectional shape of said bioartificial guidance conduit is ellipse.

25. The method for forming a bioartificial guidance conduit in claim 24, wherein the length of major axis and minor axis of the ellipse ranges from 1 mm to 5 mm.

26. The method for forming a bioartificial guidance conduit in claim 15, wherein the cross sectional area of said penetrating hole ranges from 100 μm2 to 106 μm2.

27. The method for forming a bioartificial guidance conduit in claim 15, further comprising a shell fabricating process to form a shell to cover said coaxially stacked plurality of discs.

28. The method for forming a bioartificial guidance conduit in claim 27, wherein the method for fabricating said shell comprises:
coating a solution onto the outer surface of said coaxially stacked plurality of discs, wherein said solution comprises a biocompatible material; and
performing a drying process to gel said solution located on said coaxially stacked plurality of discs, and said shell is then formed.

29. The method for forming a bioartificial guidance conduit in claim 27, wherein the method for fabricating said shell comprises:
coating a solution onto the outer surface of said coaxially stacked plurality of discs to form a intermediate conduit, wherein said solution comprises a biocompatible material; and
performing a phase separation process to soak said intermediate conduit into a nonsolvent, so as to gel said solution located on said coaxially stacked plurality of discs, and said shell is then formed.

30. The method for forming a bioartificial guidance conduit in claim 27, wherein the method for fabricating said shell comprises:
providing a plate-shaped biocompatible material;
wrapping said plate-shaped biocompatible material around said coaxially stacked plurality of discs; and
performing a binding process to connect the outer surface of said coaxially stacked plurality of discs with said plate-shaped biocompatible material, so as to form said shell.

31. The method for forming a bioartificial guidance conduit in claim 15, wherein the material of said shell is selected as any one or any combination of the following group: chitosan, poly (lactic acid), poly (glycolic acid) [PGA], poly (glycolide co-lactide) [PLGA], collage, polycarboxylic acid, alginate, polyamide and their derivatives.

32. A method for forming a bioartificial guidance conduit, comprising:
providing a substrate with a photoresist layer;
performing a lithographic process on said photoresist layer to form a first mold that comprises at least one first pattern having a raised flat-top structure and at least one second pattern having a plurality of tubular holes extending into said substrate from said raised flat-top structure, wherein the height of said raised flat-top structure is substantially equal to the depth of said tubular hole;
performing a remolding process by said first mold and a flexible material to fabricate a second mold, wherein said second mold comprises a third pattern complementary to said first pattern and a fourth pattern complementary to said second pattern, and the height of said third pattern is substantially equal to the height of said fourth pattern;
performing a mold-filling process to fill said second mold with a biocompatible material, so as to form at least one disc, wherein the main body of said disc is formed by said third pattern, and at least one penetrating hole of said disc is formed by said fourth pattern;
performing a mold-releasing process to take out at least one said disc;
repeating said mold-filling process and said mold-releasing process to produce a plurality of said discs; and
performing a coaxially stacking process to stack said plurality of discs, so as to form said bioartificial guidance conduit, wherein at least one said penetrating hole on adjacent said plurality of discs connects with each other, so as to run through said bioartificial guidance conduit, wherein the decomposing rate of said disc located at the middle of said bioartificial guidance conduit being slower than the decomposing rate of said disc located at the two ends of said bioartificial guidance conduit.

33. The method for forming a bioartificial guidance conduit in claim 32, wherein said first flexible material and said second flexible material are independently selected from the following group: poly(dimethyl siloxane) [PDMS], polyurethane.

34. The method for forming a bioartificial guidance conduit in claim 32, wherein the material of said biocompatible material is selected as any one or any combination of the following group: chitosan, poly (lactic acid), poly (glycolic acid) [PGA], poly (glycolide co-lactide) [PLGA], collage, polycarboxylic acid, alginate, polyamide and their derivatives.

35. The method for forming a bioartificial guidance conduit in claim 32, wherein the thickness of said disc ranges from 10 μm to 500 μm.

36. The method for forming a bioartificial guidance conduit in claim 32, wherein the cross-sectional area of said bioartificial guidance conduit ranges from 1 mm2 to 25 mm2.

37. The method for forming a bioartificial guidance conduit in claim 32, wherein the cross-sectional shape of said bioartificial guidance conduit is not perfect circle.

38. The method for forming a bioartificial guidance conduit in claim 32, wherein the cross-sectional shape of said bioartificial guidance conduit is ellipse.

39. The method for forming a bioartificial guidance conduit in claim 38, wherein the length of major axis and minor axis of the ellipse ranges from 1 mm to 5 mm.

40. The method for forming a bioartificial guidance conduit in claim 32, wherein the cross sectional area of said penetrating hole ranges from 100 μm2 to 106 μm2.

41. The method for forming a bioartificial guidance conduit in claim 32, further comprising a shell fabricating process to form a shell to cover said coaxially stacked plurality of discs.

42. The method for forming a bioartificial guidance conduit in claim 41, wherein the method for fabricating said shell comprises:
coating a solution onto the outer surface of said coaxially stacked plurality of discs, wherein said solution comprises a biocompatible material; and
performing a drying process to gel said solution located on said coaxially stacked plurality of discs, and said shell is then formed.

43. The method for forming a bioartificial guidance conduit in claim 41, wherein the method for fabricating said shell comprises:

coating a solution onto the outer surface of said coaxially stacked plurality of discs to form a intermediate conduit, wherein said solution comprises a biocompatible material; and performing a phase separation process to soak said intermediate conduit into a nonsolvent, so as to gel said solution located on said coaxially stacked plurality of discs, and said shell is then formed.

44. The method for forming a bioartificial guidance conduit in claim 41, wherein the method for fabricating said shell comprises:

providing a plate-shaped biocompatible material;

wrapping said plate-shaped biocompatible material around said coaxially stacked plurality of discs; and performing a binding process to connect the outer surface of said coaxially stacked plurality of discs with said plate-shaped biocompatible material, so as to form said shell.

45. The method for forming a bioartificial guidance conduit in claim 32, wherein the material of said shell is selected as any one or any combination of the following group: chitosan, poly (lactic acid), poly (glycolic acid) [PGA], poly (glycolide co-lactide) [PLGA], collage, polycarboxylic acid, alginate, polyamide and their derivatives.

* * * * *